US00PP15297P2

(12) United States Plant Patent
Olesen et al.

(10) Patent No.: US PP15,297 P2
(45) Date of Patent: Nov. 9, 2004

(54) FLORIBUNDA PLANT 'POULCS003'

(50) Latin Name: *Rosa hybrida*
Varietal Denomination: POULcs003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 93 days.

(21) Appl. No.: 10/342,697

(22) Filed: Jan. 14, 2003

(51) Int. Cl.[7] ..... A01H 5/00
(52) U.S. Cl. ..... Plt./145
(58) Field of Search ..... Plt./145

*Primary Examiner*—Bruce R. Campell
*Assistant Examiner*—Susan B. McCormick

(57) ABSTRACT

A new floribunda garden rose plant which has abundant, peach flowers and attractive foliage. This new and distinct variety has shown to be uniform and stable in the resulting generations from asexual propagation.

1 Drawing Sheet

Classification: Botanical: *Rosa hybrida* 'POULcs003'. Commercial: Floribunda rose.

SUMMARY OF THE INVENTION

The present invention constitutes a new and distinct variety of garden rose plant which originated from a controlled crossing between 'POULmulti', described and illustrated in U.S. Plant patent application No. 10/209,634 filed on Jul. 30, 2002 and an unnamed seedling. The two parents were crossed during the summer of 1993 and the resulting seeds were planted in a controlled environment in Fredensborg, Denmark. The new variety is named 'POULcs003'.

The new variety may be distinguished from its pollen parent, 'POULmulti' by the following combination of characteristics:

1. The pollen parent has the general tonality of open flowers of Yellow Group 4A and 4D while 'POULcs003' has the general tonality of open flowers of Orange Group 24D.
2. The pollen parent has an average open flower diameter of 35 to 40 mm while 'POULcs003' has an average open flower diameter of 70 to 80 mm.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULcs003' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULcs003' was selected in the spring 1994 by the inventors as a single plant from the progeny of the aforementioned hybridization.

Asexual reproduction of 'POULcs003' by traditional budding and rooted cuttings was first done by L. Pernille and Mogens N. Olesen in their nursery in Fredensborg, Denmark in August, 1994. This initial and other subsequent asexual propagations conducted in controlled environments have demonstrated that the characteristics of 'POULcs003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs003'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULcs003', as observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULmulti', a rose variety from the same inventors described and illustrated in U.S. Plant patent application No. 10/209,634 filed on Jul. 30, 2002, are compared to 'POULcs003' in Chart 1.

CHART 1

| | 'POULcs003' | 'POULmulti' |
|---|---|---|
| Open flower diameter | 70 to 80 mm | 35 to 40 mm |

CHART 1-continued

| | 'POULcs003' | 'POULmulti' |
|---|---|---|
| Color of flower petals after openings | Yellow Orange Group 18B and 18C | Yellow Group 4A and 4D |
| Anthocyanin | None observed | Present on margins of juvenile leaflets. |

Parents:

*Seed parent.*—Unnamed seedling.

*Pollen parent.*—*'POULmulti'*.

FLOWER AND FLOWER BUD

Blooming habit: Recurrent.

Flower bud:

*Size.*—Upon opening, 30 to 35 mm in length from base of receptacle to end of bud.

*Bud form.*—Long.

*Bud color.*—As sepals unfold, petals surfaces are Orange Group 24C with intonations of Yellow Group 3C. At ¼ opening petal surfaces are Orange Group 24C and 24D with intonations of Orange Group 5A.

*Sepals.*—Yellow Green Group 144A. Strong foliaceous appendages on three of the five sepals. Surfaces of sepals moderately pubescent. Stipitate glands are present along the margins and on lower surfaces of the sepals. Shape: Sepal apex is cirrose. Base is flat at union with peduncle. Size: 25 to 30 mm long×8 to 10 mm wide.

*Receptacle.*—Surface: Smooth. Shape: Funnel shaped. Size: Small. 8 mm (h)×5 mm (w). Color: Yellow Green Group 144B.

*Peduncle.*—Surface: Fragrant stipitate glands observed. Length: 35 to 40 mm average length. Color: Yellow Green Group 144B. Strength: Somewhat strong.

*Borne.*—In small clusters of 3 to 8 per stem.

*Anthocyanin.*—Color: Occurrence of Greyed Red Group 181A limited to stipitate glands.

Flower bloom:

*Fragrance.*—Light.

*Duration.*—The blooms have a duration on the plant of approximately 7 to 10 days. Petals fall cleanly away from plant.

*Size.*—Average flower diameter is 70 to 80 mm when open.

*Form.*—Shape of flower when viewed from the side: Upon opening, upper part: Flattened convex. Upon opening, lower part:Concave. Open flower, upper part: Convex. Open flower, lower part: Concave.

*Petalage.*—Double. Average range: 20 to 40 petals under normal conditions with 5 to 7 petaloids.

Color:

*Upon opening, petals.*—Outermost petals: Outer side: Yellow Orange Group 18B and 18C. Inner Side: Yellow Orange Group 19B. Innermost petals: Outer side: Orange Group 24D. Inner Side: Yellow Orange Group 18B.

*Upon opening, basal petal spots.*—Outermost petals: Outer side: Yellow Group 6C. Inner Side: Yellow Group 6C. Innermost petals: Outer side: Yellow Group 6C. Inner Side: Yellow Group 6C.

*After opening, petals.*—Outermost petals: Outer side: Yellow Orange Group 18B and 18C. Inner Side: Yellow Orange Group 18B and 18C. Innermost petals: Outer side: Yellow Orange Group 18B and 18C. Inner Side: Yellow Orange Group 18B and 18C.

*After opening, basal petal spots.*—Outermost petals: Outer Side: Yellow Group 6A. Inner Side: Yellow Group 6A. Innermost petals: Outer Side: Yellow Group 6A. Inner Side: Yellow Group 6A.

General tonality: On open flower Orange Group 24D. No change in the general tonality at the end of the 6th day. Afterwards, general tonality is Yellow Orange Group 19D.

Petals:

*Petal reflex.*—Very Slightly.

*Petal edge.*—Entire with notch in the center of the petal margin.

*Shape.*—Obovate shaped.

*Petaloids.*—Present. Quantity: 5 to 7.

*Thickness.*—Average.

*Arrangement.*—Not Formal.

Reproductive organs:

*Pistils.*—Length: 3 to 4 mm long. Quantity: 18.

*Pollen.*—Color: Greyed Orange Group 163A. Quantity: Average.

*Anthers.*—Size: 1 mm long. Color: Greyed Oranged Group 165A. Quantity: 38.

*Filaments.*—Color: Yellow Group 5A. Length: 8 to 12 mm.

*Stigmas.*—Inferior in location to anthers. Color: Greyed Yellow Group 160D.

*Styles.*—Color: Yellow Green Group 145D. Other intonations: Red Group 47C.

*Hips.*—None Observed.

PLANT

Plant growth: Compact and bushy. When grown as a nursery plant on its own roots the average plant height is 60 to 100 cm and the average plant width is 60 cm.

Stems:

*Color.*—Young wood: Yellow Green Group 144A. Older wood: Yellow Green Group 144A.

*Thorns.*—Incidence: 3 to 5 thorns per 10 cm of stem. Size: Average length: 8 to 10 mm. Color: Greyed Yellow Group 160A. Shape: Upper side is linear while lower side is concave.

*Surface.*—Young wood: Smooth. Older wood: Rough.

Plant foliage: Normal number of leaflets on normal leaves in middle of the stem: 5 leaflets.

*Leaf size.*—110 mm (l)×75 to 80 mm (w).

*Quantity.*—Average.

*Color.*—Mature Foliage: Upper leaf surface: Green Group 137A. Lower leaf surface: Green Group 137C. Juvenile foliage: Upper leaf surface: Yellow Green Group 144A. Lower leaf surface: Yellow Green Group 144B. Anthocyanin intonation: None observed.

Plant leaves and leaflets:

*Stipules.*—Size: 18 to 20 mm (l)×5 mm (w). Color: Yellow Green Group 144B with 144A at margins. Stipitate glands along the leaf margin. Anthocyanin: None observed.

*Petiole.*—Length: 12 to 15 mm in length. Color: Green Group 137A. Underneath: Yellow Green Group 144A. Margins: Stipitate glands present.

*Rachis.*—Color: Green Group 137A. Underneath: Yellow Green Group 144A. Margins: Stipitate glands present.

*Leaflet.*—Edge: Serrated. Shape: Ovate. Texture: Glossy. Arrangement: Odd pinnate. Venation: Reticulate.

Disease resistance: Above average resistance to mildew, rust, black spot, and Botrytis under normal growing conditions in Jackson County, Oreg.

Cold hardiness: The variety 'POULcs003' has been found to be cold tolerant to USDA hardiness zone 7 in Jackson County, Oreg.

We claim:

1. A new and distinct variety of rose plant of the Floribunda rose class, substantially as herein illustrated and described as a distinct and novel rose variety due to its abundant peach flowers, disease resistance, and extended period of bloom.

* * * * *

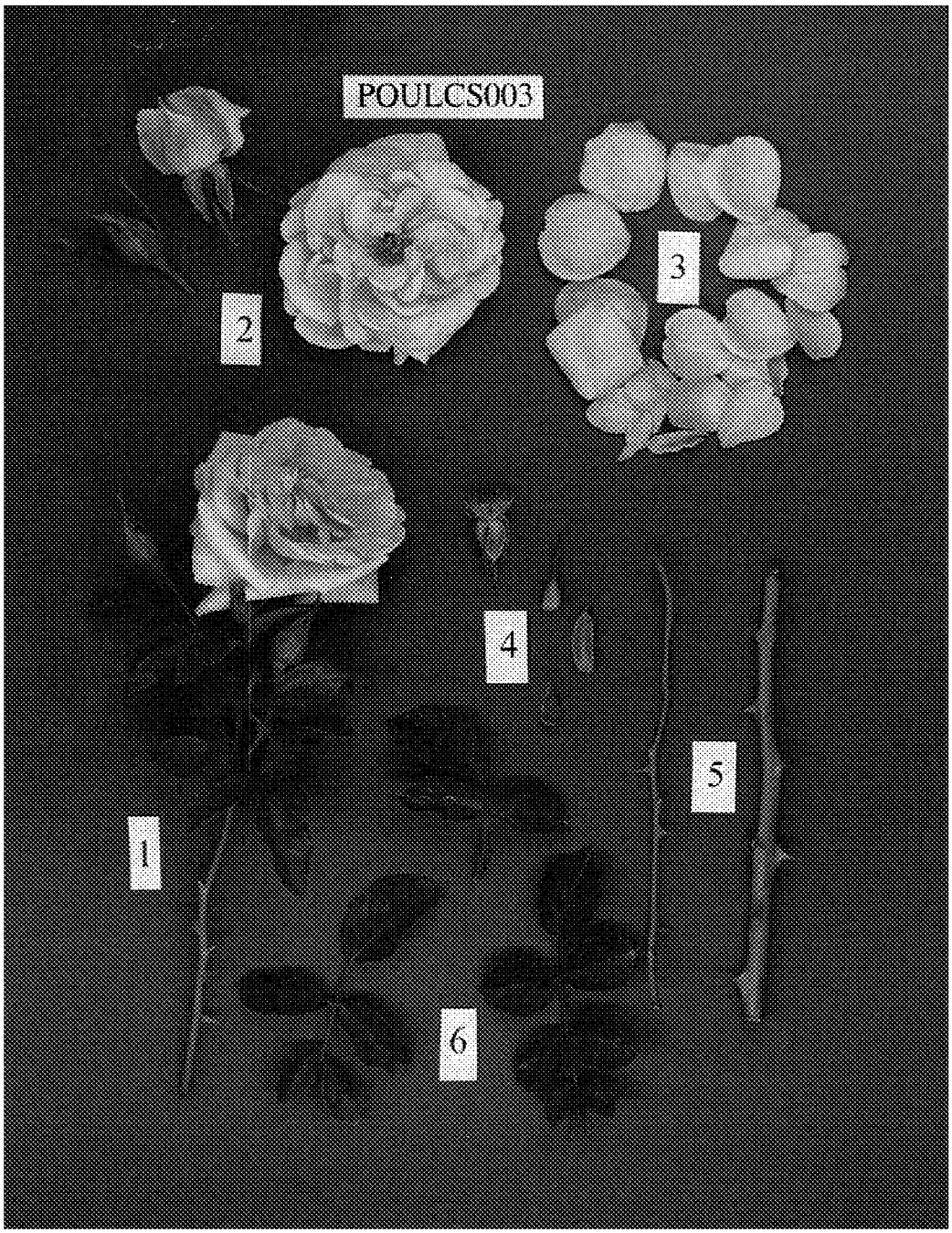
POULCS003
1
2
3
4
5
6